US00PP20585P2

(12) United States Plant Patent
Parthasarathy et al.

(10) Patent No.: US PP20,585 P2
(45) Date of Patent: Dec. 15, 2009

(54) ***AGLAONEMA* PLANT NAMED 'LILLIPUT'**

(50) Latin Name: *Aglaonema hybrida*
Varietal Denomination: Lilliput

(75) Inventors: Gopalaswamy Parthasarathy, Bangalore (IN); Parthasarathy Mukundan, Bangalore (IN)

(73) Assignee: KSG's Farm + Nursery, Alwarpet, Chennai (IN)

( * ) Notice: Subject to any disclaimer, the term of this patent is extended or adjusted under 35 U.S.C. 154(b) by 0 days.

(21) Appl. No.: 12/287,345

(22) Filed: Oct. 8, 2008

(51) Int. Cl.
*A01H 5/00* (2006.01)

(52) U.S. Cl. ..... Plt./376

(58) Field of Classification Search ..... Plt./376
See application file for complete search history.

*Primary Examiner*—Susan B McCormick Ewoldt
(74) *Attorney, Agent, or Firm*—C. A. Whealy

(57) ABSTRACT

A new and distinct cultivar of *Aglaonema* plant named 'Lilliput', characterized by its compact and outwardly arching plant habit; freely clumping habit; relatively short internodes; dense and bushy growth habit; and narrowly lanceolate leaves with dark green and silver-colored markings and dark green-colored margins.

1 Drawing Sheet

Botanical designation: *Aglaonema hybrida.*
Cultivar denomination: 'Lilliput'.

BACKGROUND OF THE INVENTION

The present invention relates to a new and distinct cultivar of *Aglaonema* plant, botanically known as *Aglaonema hybrida* and hereinafter referred to by the name 'Lilliput'.

The new *Aglaonema* is the product of a controlled breeding program conducted by the Inventors in Chamrajpet, Bangalore, India. The objective of the breeding program is to create new full and compact *Aglaonema* cultivars with good plant vigor, interesting and unique leaf forms and coloration, resistance to pathogens and pests, and tolerance to low temperatures.

The new *Aglaonema* plant is the product of a cross-pollination conducted by the Inventors on Feb. 21, 1995 of *Aglaonema commutatum* var. *picturatum* 'Silver Ribbons', disclosed in U.S. Plant Pat. No. 12,985, as the female, or seed, parent with an unnamed selection of *Aglaonemaphilippinense* var. *stenophyllum*, not patented, as the male, or pollen, parent. The new *Aglaonema* plant was discovered and selected by the Inventors in January, 1997 as a single plant from within the resultant progeny of the stated cross-pollination in a controlled environment in Chamrajpet, Bangalore, India.

Asexual reproduction of the new *Aglaonema* plant by cuttings and divisions in a controlled environment in Chamrajpet, Bangalore, India since April, 1997 has shown that the unique features of this new *Aglaonema* are stable and reproduced true to type in successive generations of asexual reproduction.

SUMMARY OF THE INVENTION

Plants of the new *Aglaonema* have not been observed under all possible environmental conditions. The phenotype may vary somewhat with variations in environment such as temperature and light intensity, without, however, any variance in genotype.

The following traits have been repeatedly observed and are determined to be the unique characteristics of 'Lilliput'. These characteristics in combination distinguish 'Lilliput' as a new and distinct cultivar of *Aglaonema:*

1. Compact and outwardly arching plant habit.
2. Freely clumping habit.
3. Relatively short internodes; dense and full growth habit.
4. Narrowly lanceolate leaves with dark green and silver-colored markings and dark green-colored margins.

Plants of the new *Aglaonema* differ from plants of the female parent, 'Silver Ribbons', in the following characteristics:

1. Plants of the new *Aglaonema* are smaller and more compact than plants of 'Silver Ribbons'.
2. Leaves of plants of the new *Aglaonema* are more narrow than leaves of plants of 'Silver Ribbons'.
3. Plants of the new *Aglaonema* have shorter petioles than plants of 'Silver Ribbons'.
4. Plants of the new *Aglaonema* and 'Silver Ribbons' differ in leaf coloration.

Plants of the new *Aglaonema* differ from plants of the male parent selection in the following characteristics:

1. Plants of the new *Aglaonema* are smaller and more compact than plants of the male parent selection.
2. Plants of the new *Aglaonema* are more freely clumping than plants of the male parent selection.
3. Plants of the new *Aglaonema* and the male parent selection differ in leaf coloration.

Plants of the new *Aglaonema* can be compared to plants of the *Aglaonema hybrida* 'Black Lance', disclosed in U.S. Plant Pat. No. 10,280. In side-by-side comparisons conducted in Chamrajpet, Bangalore, India, plants of the new *Aglaonema* differed from plants of 'Black Lance' in the following characteristics:

1. Plants of the new *Aglaonema* were more compact than plants of 'Black Lance'.
2. Plants of the new *Aglaonema* were more outwardly arching than and not as upright as plants of 'Black Lance'.
3. Plants of the new *Aglaonema* had smaller leaves than plants of 'Black Lance'.

4. Plants of the new *Aglaonema* and 'Black Lance' differed in leaf coloration.

Plants of the new *Aglaonema* can be compared to plants of the *Aglaonema hybrida* 'White Lance', disclosed in U.S. Plant Pat. No. 11,053. In side-by-side comparisons conducted in Chamrajpet, Bangalore, India, plants of the new *Aglaonema* differed from plants of 'White Lance' in the following characteristics:

1. Plants of the new *Aglaonema* were more compact than plants of 'White Lance'.
2. Plants of the new *Aglaonema* had smaller leaves than plants of 'White Lance'.
3. Plants of the new *Aglaonema* and 'White Lance' differed in leaf coloration.

BRIEF DESCRIPTION OF THE PHOTOGRAPH

The accompanying photograph illustrates the overall appearance of the new *Aglaonema*. This photograph shows the colors as true as it is reasonably possible to obtain in colored reproductions of this type. Colors in the photograph may differ slightly from the color values cited in the detailed botanical description which accurately describe the colors of the new *Aglaonema*. The photograph is a top perspective view of a typical plant of 'Lilliput' grown in a container.

DETAILED BOTANICAL DESCRIPTION

The aforementioned photograph and following observations and measurements describe plants grown in 15-cm containers in Miami, Fla. during the summer in a polypropylene-covered shadehouse. Plants were grown under conditions and practices which approximate those generally used in commercial *Aglaonema* shadehouse production. During the production of the plants, day temperatures ranged from 27° C. to 37° C., night temperatures ranged from 15° C. to 26° C. and light levels averaged 1,500 foot-candles. Plants had been growing for 15 months when the photograph and the detailed description were taken. In the following description, color references are made to The Royal Horticultural Society Colour Chart, 2001 Edition, except where general terms of ordinary dictionary significance are used.

Botanical classification: *Aglaonema hybrida* 'Lilliput'.

Parentage:

*Female, or seed, parent.*—*Aglaonema commutatum* var. *picturatum* 'Silver Ribbons', disclosed in U.S. Plant Pat. No. 12,985.

*Male, or pollen, parent.*—Unnamed selection of *Aglaonema philippinense* var. *stenophyllum*, not patented.

Propagation:

*Type.*—By cuttings.

*Time to initiate roots, summer.*—About 21 to 28 days at 25° C. to 32° C.

*Time to initiate roots, winter.*—About 30 to 40 days at 12° C. to 25° C.

*Time to produce a rooted young plant, summer.*—About 30 to 35 days at 25° C to 32° C.

*Time to produce a rooted young plant roots, winter.*—About 45 to 60 days at 12° C. to 25° C.

*Root description.*—Fleshy, medium in thickness; off-white in color.

*Rooting habit.*—Freely branching; dense and profuse.

Plant description:

*Plant and growth habit.*—Compact and outwardly arching plant habit; freely clumping habit; short internodes; full and dense habit; moderately vigorous growth habit; suitable for 15-cm containers. Developing leaves initially upright, then arching outwardly with development.

*Plant height, from soil level to top of leaf plane.*—About 24 cm.

*Plant diameter or spread.*—About 47 cm.

*Stem description.*—Clumping habit: Plants of the new *Aglaonema* are freely clumping with about ten clumps developing per plant. Aspect: Mostly upright. Strength: Strong; somewhat flexible. Length, soil level to junction to two youngest leaves: About 3 cm. Diameter: About 1.1 cm. Internode length: About 5 mm. Color: Close to 144A. Cataphylls: Not observed.

Foliage description:

*Arrangement.*—Alternate/whorled; simple.

*Length.*—About 18.5 cm.

*Width.*—About 3.5 cm.

*Shape.*—Lanceolate.

*Apex.*—Acuminate; recurved.

*Base.*—Obtuse.

*Margin.*—Entire; slightly undulate.

*Texture, upper and lower surfaces.*—Smooth, glabrous.

*Venation pattern.*—Pinnate.

*Color.*—Developing leaves, upper surface: Ground color, more green than 146A; random markings, close to 148A, 148B and 148C; margins, more green than 146A. Developing leaves, lower surface: Close to 146A to 146B. Fully expanded leaves, upper surface: Ground color, between 139A and N137A; random markings, close to 189A, 191A to 191B and 194A to 194B; margins, between 139A and N137A; venation, similar to surface coloration.

Fully expanded leaves, lower surface: Close to 146A to 146B; underlain markings, close to 147B to 147C; venation, similar to surface coloration.

*Petiole.*—Aspect: Mostly erect, outwardly arching with development. Length: About 10 cm. Diameter, distal: About 3 mm. Diameter, proximal, flattened: About 1.2 cm. Strength: Strong; flexible. Color, distal: Close to 147A. Color, proximal: Close to 147B to 147C; random flecking, close to 157A to 157C; area adjacent to stem, close to 157A to 157C. Wing length: About 7.5 cm. Wing diameter, base: About 2 cm. Wing color, inner and outer surfaces: 147A to 147C; area adjacent to stem, close to 157A to 157C.

Inflorescence description: Inflorescence development has not been observed on plants of the new *Aglaonema*.

Disease/pest resistance: Plants of the new *Aglaonema* have not been observed to be resistant to pathogens or pests common to *Aglaonema*.

Temperature tolerance: Plants of the new *Aglaonema* have been observed to be tolerant to temperatures ranging from about 15° C. to about 40° C.

It is claimed:

1. A new and distinct *Aglaonema* plant named 'Lilliput' as illustrated and described.

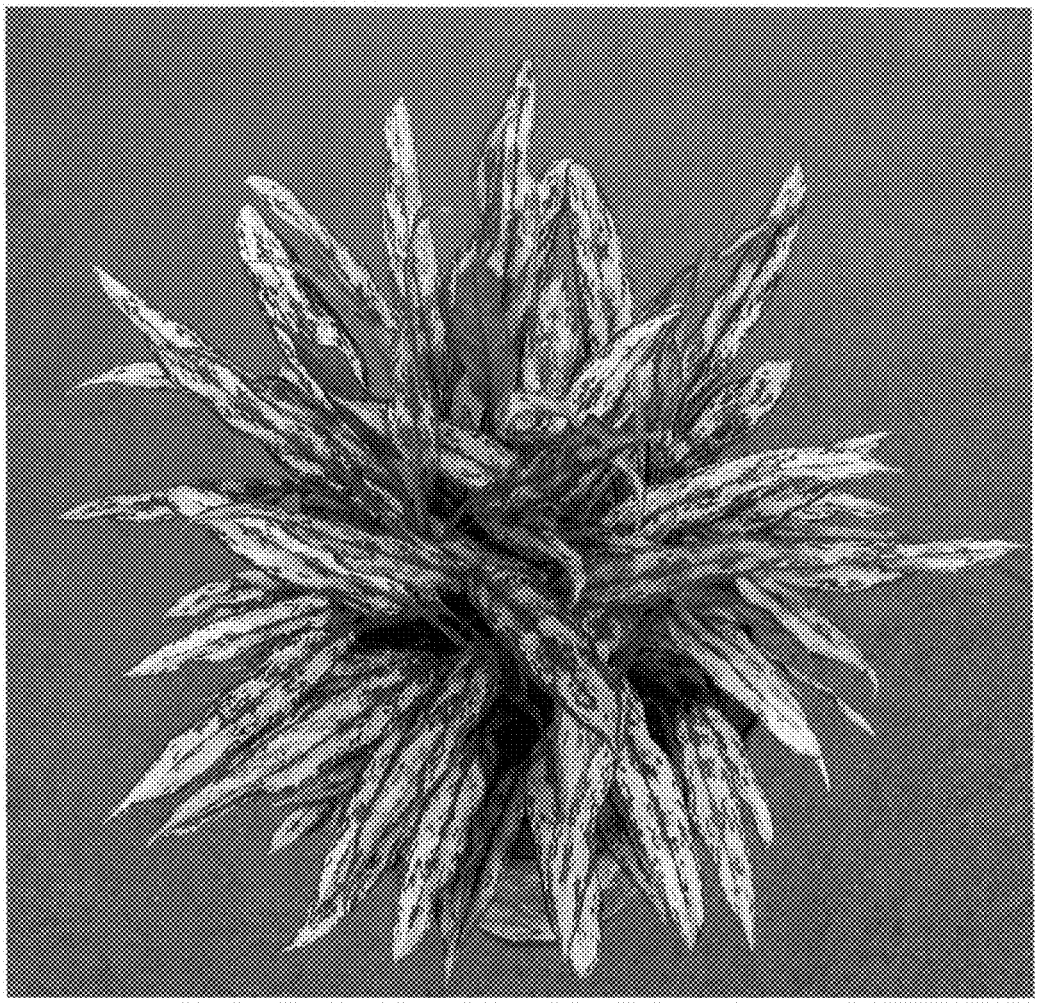

* * * * *